US005361755A

United States Patent [19]
Schraag et al.

[11] Patent Number: 5,361,755
[45] Date of Patent: Nov. 8, 1994

[54] METHOD AND APPARATUS FOR MEDICAL MONITORING

[75] Inventors: Martin Schraag, Sindelfingen; Andreas Boos, Bondorf, both of Germany

[73] Assignee: Hewlett-Packard Company, Palo Alto, Calif.

[21] Appl. No.: 12,328

[22] Filed: Feb. 2, 1993

[51] Int. Cl.$^5$ ............................................. A61B 5/00
[52] U.S. Cl. ...................................................... 128/630
[58] Field of Search .............. 128/630, 632, 633, 637, 128/670, 680, 681, 687–690, 693, 700, 706, 707, 709, 714, 903, 904, 906, 741; 607/32; 340/573

[56] References Cited

U.S. PATENT DOCUMENTS

| | | | |
|---|---|---|---|
| 4,268,179 | 5/1981 | Long et al. | 400/120 |
| 5,056,059 | 10/1991 | Tivig | 364/900 |
| 5,207,642 | 5/1993 | Orkin et al. | 604/65 |
| 5,215,100 | 6/1993 | Spitz et al. | 128/741 |

FOREIGN PATENT DOCUMENTS

3729760A1  6/1989  Germany ............... A61B 5/10

Primary Examiner—William E. Kamm
Assistant Examiner—Marianne Parker

[57] ABSTRACT

A medical monitor, such as a fetal monitor, is provided with a code reader, e.g. a bar code reader. A manual contains clear text instructions as well as predefined codes in their correct sequential form. The instructions help the unskilled user to operate the monitor, and the actual monitor functions are triggered by scanning the codes, instead of pushing buttons, turning knobs etc. A questionnaire may also be provided to enter answers to anamnesis data. These answers, together with vital signs data, may be transmitted via telephone lines to a hospital, which makes the medical monitor ideally suited for home monitoring applications.

23 Claims, 3 Drawing Sheets

2. QUESTIONNAIRE

1. DID YOU LOOSE BLOOD?    YES    NO    DON'T KNOW

2. DO YOU FEEL LABOR?    YES    NO    DON'T KNOW

3. DO YOU FEEL PAIN?    YES    NO

I. MANUAL

1. MONITOR INSTALLATION
....

2. MEASUREMENT:
   - SWITCH ON MONITOR
   - APPLY TRANSDUCERS (OPTIMAL SIGNAL OF ULTRASOUND TD)
   - ADJUST VOLUME

- START MEASUREMENT AND RECORDING

GREEN LAMP MUST BLINK NOW

RESPOND NOW TO ALL QUESTIONS OF THE ENCLOSED QUESTIONNAIRE

STOP RECORDING AFTER 30 MINUTES:

3. TRANSMISSION:
   CONNECT MONITOR WITH TELEPHONE JACK
   START TRANSMISSION NOW:

YELLOW LAMP MUST BLINK NOW
   ...

METHOD AND APPARATUS FOR MEDICAL MONITORING

FIELD OF THE INVENTION

The present invention relates to methods for operating medical monitors. It also covers the monitors themselves. More specifically, the invention addresses problems encountered with operation of medical monitors by unqualified personnel—e.g., the patient itself in so-called "home monitoring" applications", in particular in the field of fetal monitoring.

BACKGROUND OF THE INVENTION

Operation of medical monitors is an issue of major importance. In most cases, such monitors are operated by personnel without technical education, such as nurses. The increasing complexity of state-of-the-art medical monitors, and the additional functionality provided by such equipment, as compared to prior art monitors, makes it necessary to focus on an easy-to-operate "man-machine" interface. In the field of medical monitoring, this is a particularly important problem, not only due to the time it takes to train a non-technical person, but also for reasons of patient safety. For example, if a nurse accidentally switches off the alarm capability of a medical monitor, this may well lead to the death of the patient.

There have already been attempts in the prior art to overcome the restrictions of the "knob and button" approach. For example, buttons not required for everyday operation of a monitor have been hidden behind a cover. Likewise, operation of the monitors has been automated, in order to reduce the amount of human interactions.

Another approach is the use of softkeys, i.e., keys without a fixed label, and with dynamically assigned function. One successful attempt to implement such a softkey concept in a medical monitor is disclosed in U.S. Pat. No. 5,056,059. This prior art human interface uses two- or three-level input sequences, wherein the meaning of the softkeys changes from level to level.

However, it will be noted that a softkey concept requires expensive hardware components, like a display (which is used to depict the various softkey labels). Therefore, the softkey approach is useful in applications which require an expensive monitor, and a display anyway (as is the case in the configurable monitor according to U.S. Pat. No. 5,056,059).

In contrast, the softkey concept does not meet the needs of small or stand-alone monitors which are not equipped with a display, and the necessary number of keys. It will be understood that it would be an extremely costly measure to provide a display simply for the purpose of labelling the softkeys.

Another attempt to make the user interface easier relies on menu-driven user interaction. That is, the user is guided through several steps, and the monitor may propose adequate measures. However, such menus require the provision of a display as well.

The above concepts are also not suited for operation by the patient himself, e.g., in home monitoring applications (i.e., a monitor located at the patient's home). Whatever operating concept is used during home monitoring, the patient will have to study complex instructions. In this context, it is particularly important to note that a medical monitor includes a multiplicity of functions which are partially sensitive to patient safety; likewise, the order of the steps is important. Consider, for example, a calibration procedure wherein the sequence of steps has to be performed in the correct order. If this order is not kept, the monitor will be incorrectly calibrated and therefore not indicate a dangerous situation of the patient.

Yet another problem associated with home monitoring is the correct anamnesis. During home monitoring, the vital signs (like the electrocardiogram, respiration, temperature etc.) are usually recorded by a remote monitor and transmitted to the hospital, or the doctor's office, via telephone lines. However, home monitoring requires not only that the vital signs of the patient are picked up by various transducers, but also some additional information which cannot be measured by a medical monitor, such as general feeling, skin color, weight etc. In the prior art, this additional information has been communicated over the phone. A person at the receiving end (doctor, nurse) recorded the answers and coded them for electronic processing. However, it will be appreciated that this process as such is very labour-intensive, costly and uncomfortable for the patient—a person recording his answers will not always be available, an extra telephone connection has to be set up, and the monitoring cycle is interrupted.

Although it would be possible to use an interactive and/or menu-driven system to record the patient's answers, this solution suffers from the same drawbacks as outlined above. That is, a display is required, the system is error-prone etc.

It is understood that this is not only a problem in home monitoring; in contrast, it applies whenever the patient provides an auto-anamnesis.

The above considerations apply particularly in cases of fetal monitoring with a "home monitor", i.e., when a fetal monitor is used in the pregnant woman's home. The well-being of the mother, pain etc. is clinically important information which cannot be transmitted to the hospital, or the obstetrician's office, in a cost-effective and convenient manner by the equipment provided by prior art solutions.

SUMMARY OF THE INVENTION

The present invention provides a new and improved method for operating a medical monitor, in particular a fetal monitor, by technically unqualified personnel and in particular by the patient himself. Likewise, the invention relates to an improved method for recording an anamnesis, in particular from a remote distance. It also deals with the apparatus required therefor.

Accordingly, it is a major object of the present invention to overcome the drawbacks of the prior art discussed above.

It is another object of the invention to provide a method and apparatus for operating a medical monitor reliably, such that no clinically important information is lost or distorted, even if operated by the patient or another untrained person. It is also an object to provide a cost-effective solution for this problem.

A related object of the invention is to provide a method of operating a medical device from a remote location where no technically and/or clinically trained personnel is available, in particular at the patient's home.

It is yet another object of the invention to provide a method and apparatus for recording the finding of a patient which does not require direct interaction of medical personnel, and which is error-tolerant and comfortable to the patient. Again, one important area of application is home monitoring.

Another object of the invention is to provide a fetal monitor which can be operated at the home of a patient reliably by himself, and to record its finding.

The method according to the invention includes the steps of

Connecting a code reading device to the monitoring device;

providing a manual with clear text instructions and predefined codes, wherein the latter represent operating functions of said monitoring device;

scanning said codes with said code reading device according to the instructions in said manual, whereby signals, in particular electrical signals, representative of said codes are transmitted to said monitoring device; and operating said monitoring device according to said signals.

The invention makes use of a manual which contains clear text instructions for the patient's attention, like "Apply transducer", and machine-readable codes which are transmitted to the medical monitor as soon as the patient (or any other person) scans the code. A common and well-known kind of code which can advantageously be used in the present invention are bar codes scanned by an optical reader. However, OCR codes (characters readable by an optical character reader), magnetic codes etc. could be used as well.

The manual—which may also be a single page, a card, a binder and the like—is thus used to give guidance to the patient, whereas the codes transmitted to the monitor control its operation. For example, take a transcutaneous gas monitor. In a simple case, the manual will e.g. instruct the patient that the monitor has to calibrated once a day, that measurements can be taken, that a record may be transmitted to the hospital, or that the time may be set.

Let us assume the patient chooses to calibrate the monitor. He will start at the chapter entitled "Calibration" and scan a corresponding code which puts the monitor in calibration mode. Next, he will be instructed to put the transducer in a reference solution, and to connect the transducer to the monitor. Once done, this is acknowledged by scanning the next code.

The patient will further be instructed to wait for, say, 2 minutes and scan yet another code. This indicates to the monitor that the calibration has been completed. The patient may then be asked to enter the barometric pressure, which can be done by scanning various codes which correspond to numerics.

It will be appreciated that other monitor functions may be performed in similar manner, and without any handling of control knobs, buttons or the like. This makes handling not only easier, but also helps the user to overcome any concerns he might have with the operation of technical equipment. This is because he has only to scan codes in a clear-text manual, which is quite similar to reading a book and highlighting portions of the text. The method is quite inexpensive to implement, e.g., using bar codes readers or optical character readers which are available on the market.

Another important consideration is that this method is safer against faulty operation than prior art methods. For example, there is no danger to operate the wrong knob or button—the patient simply focuses on the next code appearing in the manual. The monitor may also control, to a certain extent, whether it is operated correctly. Assume, for example, a calibration process wherein a transducer has to be kept in a reference solution until its reading becomes stable. Whenever the patient indicates the end of the calibration process by scanning the corresponding code and a predefined time limit—say, 1 minute—has not expired since the start of the calibration, the monitor may conclude that it has been operated improperly, and reject the calibration.

It is another important advantage of the inventive method that it can be easily adapted to a home monitoring embodiment wherein data are transmitted to a hospital, or a doctor's office, via telephone lines. Telephone transmission of readings taken up by a transducer is already prior art, see, for example, DE-A-37 29 760. However, the present invention offers the possibility to perform such transmission more reliably, and at lower cost, than with prior art equipment. In particular, the patient may be guided through a data acquisition process and, after its completion, be asked to set up the telephone connection. Thus, the data may be transmitted as a package, which requires only short connection times and is thus considerably cheaper. Other information, like monitor status, may also be included. Further, the patient will always choose the start of the transmission at the correct point in time. It is understood, however, that a permanent telephone connection, with uninterrupted transmission of data, may be set up as well.

The above method is particularly suited for fetal monitoring, just because home monitoring is a perfect solution for high-risk gestation which requires frequent recordings of the fetal heart rate, as well as maternal labor, to be taken. However, prior art approaches to implement fetal home monitoring have not been very successful, due to complicated and error-prone operation of the monitor. The invention provides a solution therefor.

Another aspect of importance for fetal home monitoring is that the pregnant woman may operate the monitor even during signal recording, when she is in lateral or dorsal position. This does not only make operation easier, but also prevents against defective recordings e.g. caused by patient movement.

Yet another advantage of the present invention is of more technical nature. That is, the codes in the manual may not only be a representation of the alphanumeric information the user wants to send to the monitor, but an encoded instruction instead. This makes it easier to adapt the manual to different languages—only the clear text has to be replaced, whereas the codes may remain. One could even use language-specific overlays which are put on a code table, the code table being the same for all countries.

This latter aspect of the present invention further allows shorter codes, which has the two-fold advantage of short transmission times, and reduction of errors upon scanning the codes (it will be appreciated that scanning long codes requires some practice).

According to another aspect of the invention, a method is provided for recording the finding of a patient including the steps of:

Connecting at least one medical transducer to the patient and to a monitoring device;

recording signals picked up by said medical transducer;

connecting a code reading device to said monitoring device;

providing a questionnaire with clear text questions and answers, wherein said answers are also provided as codes readable by said code reading device;

scanning said codes with said code reading device, whereby signals, in particular electrical signals, representative of said codes are transmitted to said monitoring device;

retrieving said signals; and retrieving and converting said codes into clear text.

This method may use a bar code reader, an optical character reader, a magnetic reader etc. as well. It deals with a related aspect of medical monitor operation, namely the acquisition of anamnesis data which cannot be directly recorded by automatic equipment, such as skin color, general feeling, pain and the like. Commonly, the acquisition of such data is performed by human personnel, which is a time-consuming and inconvenient process, in particular if the patient is located remote from the hospital or the doctor's office, like in home monitoring applications. If electronic anamnesis data processing is provided, the finding of the human interviewing the patient has to be electronically encoded, in addition to the interview itself.

The invention deals with these aspects as it provides a method for acquisition of anamnesis data which can be performed by the patient himself, although he has no knowledge about the clinical meaning of the questions, nor would he be able to enter his data via a keyboard or the like into an electronic data processing system. For this purpose, a questionnaire is submitted to him with the necessary questions in clear text. The answers are given, and read by a monitoring device, by scanning preprinted codes which also carry their meaning in clear text. For example, a simple question like "Do you feel pain ?" could be answered as "Yes", "No", "Don't know" or "Don't understand the question". These answers are preprinted in clear text, as well as optically, magnetically, electronically etc. readable codes which are simply struck by the patient, in response to the question.

At the same point in time, the patient's vital signs are recorded by the monitoring device such that a complete anamnesis record is generated.

It is understood that this aspect of the invention provides the same and similar advantages as the first embodiment discussed above, such as convenient data pick-up when the patient is in lateral position, low cost, easy transmission upon home monitoring etc. The latter aspect is of particular importance as there is no longer a need for extensive telephone conversations with a doctor, nurse or midwife when standard data are collected.

It will further be understood that the inventive method is not only useful for the patient, but may also be used by medical personnel. For example, if a nurse interviews a patient, she may use the method and apparatus according to the invention for an instantaneous record, such that no further data entry is necessary.

Of particular importance is a combination of both aspects of the present invention. Consider, for example, a fetal home monitor. The first aspect of the invention is then useful to operate the fetal monitor, and the second to record general anamnesis data which may later be transmitted to a hospital or an obstetrician's office via modems and telephone lines.

BRIEF DESCRIPTION OF THE DRAWINGS

The invention will now be explained, by means of a non-limiting example, with reference to the accompanying drawings, in which:

FIG. 3 shows a manual with clear text and codes, as well as a code reader, FIG. 4 is an example of an operating manual and FIG. 5 depicts an example of a questionnaire.

DETAILED DESCRIPTION OF THE PREFERRED EMBODIMENTS

Figure 1:
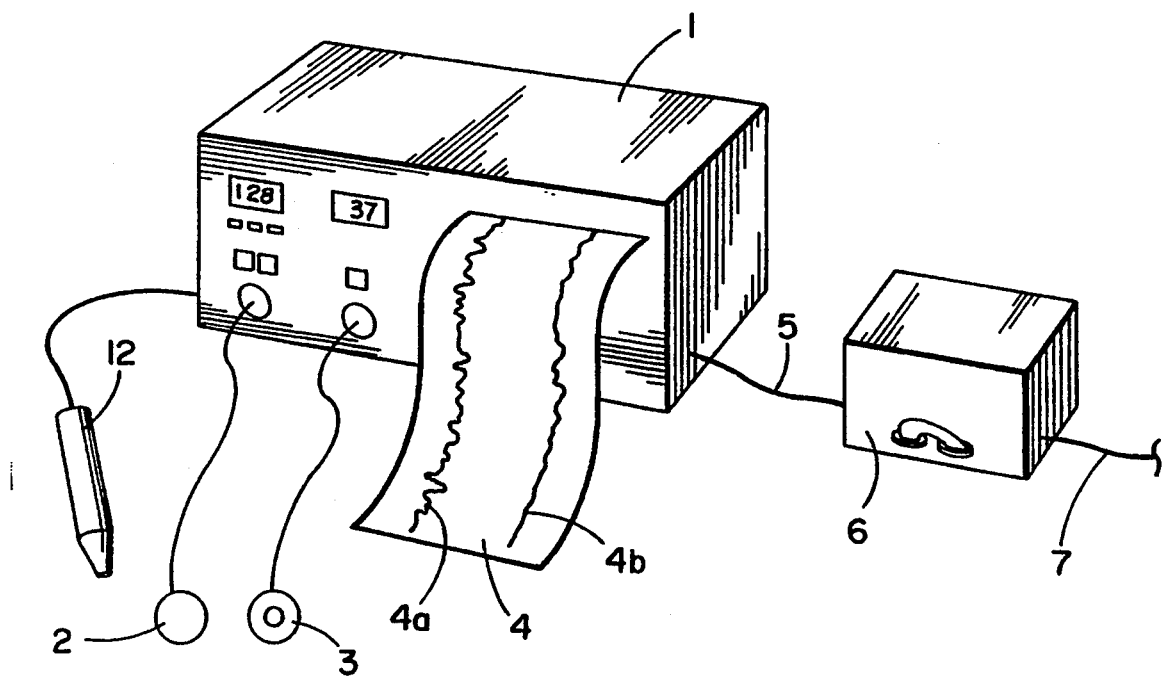
FIGS. 1 and 2 depict a fetal monitor for home monitoring applications, as well as its connection to a central station located in a hospital.

FIG. 1 depicts a fetal monitor 1 including two transducers 2 and 3. Transducer 2 is a fetal heart rate transducer; most commonly, it will be an ultrasound transducer, although there exist other techniques for recording the fetal heart rate as well (direct ECG, fetal heart sound etc.). Likewise, transducer 3 is a toco transducer recording maternal labor. This transducer may be placed on the maternal abdomen and may include a tension-measuring device, such as a resistive strain gauge.

Monitor 1 further comprises various digital displays, and some operating buttons which are prior art and will therefore not be discussed in detail herein. A recorder 4, e.g., a thermal printer, records the fetal beat-to-beat heart rate trace (4a) and maternal labor (4b). Monitor 1 may include other prior art features such as a system interface, or the like.

A connection line 5 connects monitor 1 with a modem 6. The modem, in turn, establishes a connection with a telephone line 7. For graphical purposes, this telephone line is not shown in its entirety. It ends (7') at another modem 8 (FIG. 2) which may be located in a hospital, a doctor's office or the like where it is connected, via line 9, with a central station or other data processing equipment. In the exemplary embodiment shown in FIG. 2, it is a computer 10, like a personal computer, and a printer 11.

FIG. 1 depicts also a bar code reader 12 connected with fetal monitor 1 which is used for monitor operation and anamnesis data entry by the patient, as will be described below.

Figure 2:
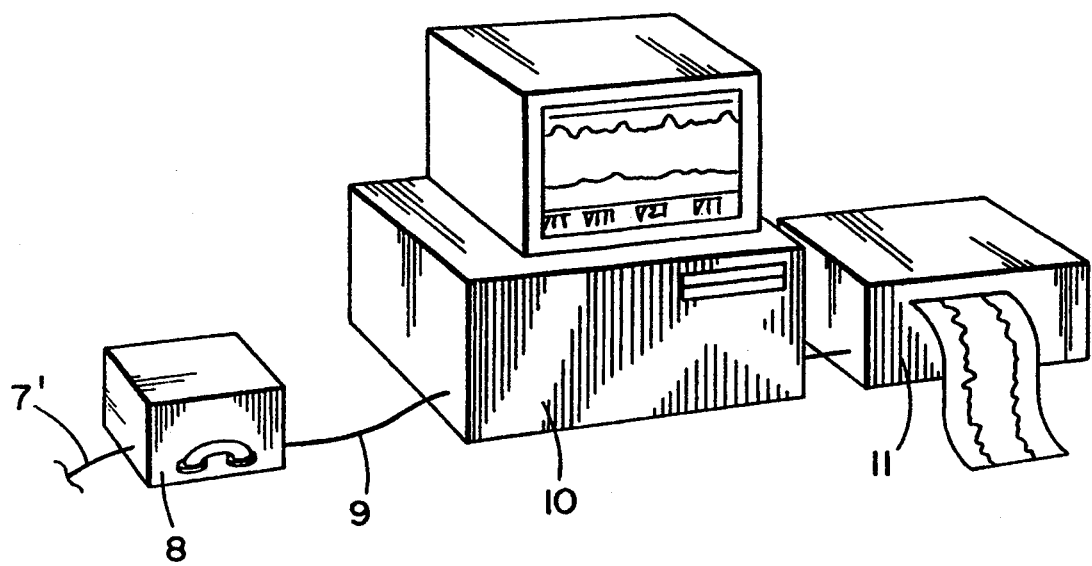

The configuration of FIGS. 1 and 2 depicts a typical home monitoring embodiment as it is used, for example, in applications where some risk exists for the mother, or the baby. It is understood that extremely high risk gestation requires that the mother is admitted to and monitored in hospital. However, there are also less risky cases wherein such a drastic measure is not necessary; however, it may be desired to monitor the pregnant woman frequently, e.g., daily. In the latter case, the expectant mother may be provided with a fetal monitor and asked to operate it at their home, as well as to transmit the recordings via telephone to the hospital in regular intervals.

It is understood that such a home monitoring application requires a monitor which is easy to operate. This is different from a fetal monitor which is operated in hospital under control of qualified and trained personnel. Further requirements are safety against faulty operation by the mother, and the possibility to record and transmit anamnesis data which cannot be recorded by automatic monitoring equipment.

These features are provided by the present invention by means of data entry via bar code reader 12. The mother does not need to operate the fetal monitor by means of knobs, buttons, softkeys or the like (although it might be necessary to push the "power on" button to start operation). Instead, a manual is provided with clear text and bar codes, wherein the latter are transmitted to the monitor as soon as they are struck.

Figures 3, 5:
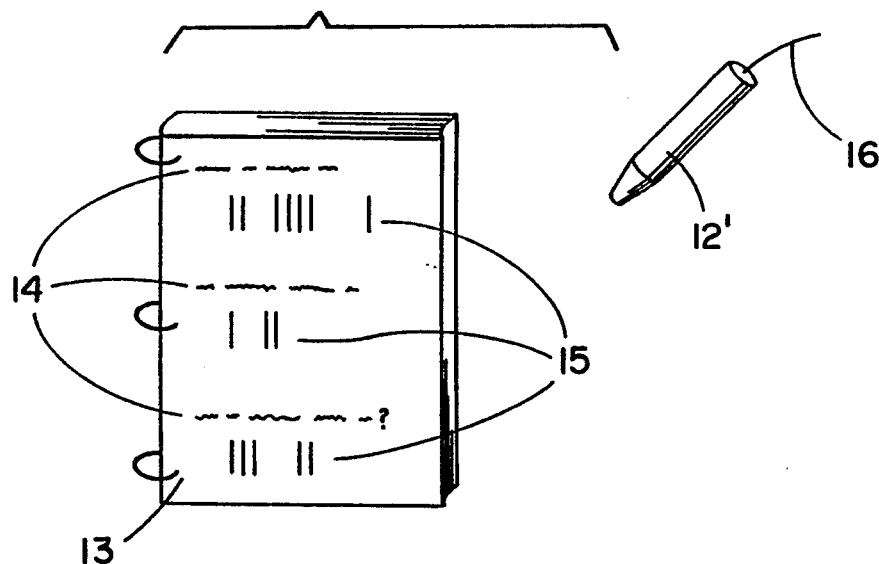

FIG. 3 depicts an example of a manual 13 which is provided to the mother, together with the fetal monitor. The manual is shown in FIG. 3 in booklet form; however, it is understood that a single page, or any other suitable medium to print clear text and bar codes, may be used as well.

The manual contains clear text 14 such as instructions for the user, as well as bar codes 15. Whenever the user scans one of the bar codes with bar code reader 12', it is transmitted, e.g. in electronic form, to the fetal monitor (not shown in FIG. 3) via cable 16.

One specific example of an operating manual is shown in FIG. 4. Whenever the pregnant woman wants to start a recording cycle, she opens the manual at the depicted page. The steps for monitor installation are not explicitly shown in FIG. 4, as installation is done only once.

The manual further contains the instructions (in clear text) about the start of a recording/measurement cycle, namely "Switch on Monitor", "Apply Transducers" and "Adjust Volume" (the latter step relates to adjustment of the loudspeaker which reflects the fetal heart beat). After all, the monitor is ready to start for measurement and recording. The start is effected by scanning the first bar code.

It will be appreciated that this is a quite convenient and error-safe process. In particular, the pregnant woman may operate the fetal monitor from her bed, with all transducers applied. Further, she is guided by the clear text in the manual. As the single steps are printed in their sequential order, the possibility of faulty monitor operation is drastically reduced. Last not least, the monitor provides feedback, in this case by turning on a blinking green lamp. This gives the mother full control over monitor operation. It is understood that an acoustic signal, like a "beep", may also be used to confirm the entry of a bar code.

The next clear-text instruction in the manual is to respond to the questions of the questionnaire. The questionnaire as shown in FIG. 5 contains several questions of general nature, such as "Do you feel pain ?". These are questions with simple responses like "Yes" or "No". Of course, it would also be possible to enter numeric values, e.g. body temperature, via an appropriate numeric bar code field; however, the above easy-to-answer questions are preferred.

Returning to FIG. 4, yet the next instruction is to stop recording after 30 minutes, by scanning the appropriate bar code. This step illustrates two further advantages of the present invention: First, the responses to the questionnaire can be provided during recording, i.e., time is saved because both tasks can be performed simultaneously. Second, the monitor may check whether it has been operated correctly; e.g., a check may be made as to whether recording has in fact lasted at least half an hour. The pregnant woman may now disconnect the transducers and get up from bed.

The third step shown in the manual of FIG. 4 is the transmission of the recorded data, as well as the responses to the questionnaire. The mother is thus asked to connect the monitor with a telephone jack, and start the transmission by scanning the appropriate bar code. Control is provided in that the monitor switches a blinking yellow lamp on.

We claim:

1. Method for operating a medical monitoring device including the steps of:
   Connecting a code reading device to said monitoring device;
   providing a manual with clear text instructions regarding operating functions of said monitoring device and predefined codes representing said operating functions of said monitoring device;
   scanning said codes with said code reading device according to the clear text instructions in said manual to cause electrical signals representative of said codes to be transmitted to said monitoring device; and
   operating said monitoring device according to said electrical signals.

2. Method according to claim 1, wherein said scanning step includes scanning said codes which are logically positioned, said codes preprinted at a logically correct position in said manual, such that a person operating said code reading device is automatically guided to operate said monitoring device correctly and said scanning step is thereby controlled to enter said codes in proper order.

3. Method according to claim 2, wherein said scanning step includes scanning said codes which are sequentially positioned, said codes preprinted in a correct sequential form for a typical operation of said monitoring device to assure that said scanning step enters said codes in proper sequential order.

4. Method according to claim 1, wherein said operating step further converts said signals into corresponding operating instructions.

5. Method according to claim 1, further including the steps of:
   connecting at least one medical transducer to a patient and to said monitoring device;
   recording signals picked up by said medical transducer.

6. Method according to claim 5, further including the steps of:
   connecting said monitoring device with a central station;
   transmitting said recorded signals to said central station.

7. Method according to claim 5, further including the steps of:
   Collecting signals and storing them in said monitoring device;
   establishing a connection via a telephone line;
   transmitting said station signals in a packet; and
   releasing said telephone line.

8. Method for recording findings of a patient including the steps of:
   Connecting at least one medical transducer to the patient and to a monitoring device;
   recording signals picked up by said medical transducer;
   connecting a code reading device to said monitoring device;
   providing a questionnaire with clear text questions and answers, said answers further provided in said questionnaire as codes readable by said code reading device;

scanning said codes with said code reading device in accordance with patient-determined answers to said clear text questions to generate electrical signals codes, and transmitting said electrical signals to said monitoring device;

retrieving said signals; and retrieving and converting said codes into clear text.

9. Method according to claim 8, wherein said steps of retrieving include the steps of:

connecting said monitoring device with a central station, transmitting said signals, as well as said codes, to said central station.

10. A kit comprising:

A code reading device;

a manual which includes clear text instructions and predefined codes which represent operating functions of said monitoring device;

a monitoring device;

means for connecting said code reading device with said monitoring device; and means in said monitoring device for receiving said predefined codes as user inputs by operation of said code reading device in accordance with said clear text instructions and decoding said predefined codes into operating instructions.

11. A kit according to claim 10, wherein said codes are preprinted at logically correct positions in said manual, such that a person operating said code reading device is automatically guided to operate said monitoring device correctly.

12. A kit according to claim 10, wherein said code reading device is a bar code reader, and said predefined codes are preprinted bar codes.

13. A kit according to claim 10, wherein said codes represents logically encoded instructions 14. A kit according to claim 10, wherein said codes are encoded in dependence of a specific monitoring device.

15. A kit according to claim 10, including at least one medical transducer for recording physiological signals of a patient.

16. A kit according to claim 15, including a connection between said monitoring device and a central station, to enable said monitoring device to transmit said physiological signals, as well as said codes, to said central station.

17. A kit according to claim 16 including a telephone line and modems.

18. A kit according to claim 10, wherein said monitoring device is a fetal monitor.

19. A kit including apparatus for recording the findings of a patient comprising:

A medical monitoring device at least one medical transducer connected to said monitoring device;

a code reading device connected to said monitoring device;

a questionnaire with clear text questions and answers, said answers also provided to codes readable by said code reading device; and means for connecting said monitoring device; to a central station, to enable said monitoring device to transmit said codes to said central station.

20. The kit according to claim 19, wherein said code reading device is a bar code reader, and said codes are preprinted bar codes.

21. A kit according to claim 19, wherein said at least one medical transducer record physiological signals of a patient and said monitoring device transmit said physiological signals to said central station.

22. The kit according to claim 21 wherein said means for connecting includes a telephone line and modems.

23. The kit according to claim 19, wherein said monitoring device is a fetal monitor.

* * * * *

UNITED STATES PATENT AND TRADEMARK OFFICE
CERTIFICATE OF CORRECTION

PATENT NO. : 5,361,755

DATED : November 8, 1994

INVENTOR(S) : Schraag et al.

It is certified that error appears in the above-identified patent and that said Letters Patent is hereby corrected as shown below:

Claim 7, col. 8, line 55 replace "station" with --stored--.

Claim 9, col. 9, line 4 after "signals" and before "codes" insert --representative of said--.

Claim 13, col. 9, line 40 replace "represents" with --represent--.

Claim 19, col 10, line 24 replace "to" with --as--.

Claim 21, col. 10, line 33 replace "record" with --records--.

Signed and Sealed this

Seventh Day of February, 1995

Attest:

BRUCE LEHMAN

Attesting Officer

Commissioner of Patents and Trademarks